United States Patent

Nady et al.

Patent Number: 6,072,080
Date of Patent: Jun. 6, 2000

[54] PURIFICATION PROCESS

[75] Inventors: Louie Akos Nady; Seyed Mehdi Tavana, both of Daphne, Ala.; Thomas Gray, Midhurst, United Kingdom; Stephen Martin Brown, Upper Cumberworth, United Kingdom; Brian David Gott, Skilmanthokee, United Kingdom

[73] Assignee: Zeneca Limited, London, United Kingdom

[21] Appl. No.: 09/041,858

[22] Filed: Mar. 12, 1998

Related U.S. Application Data

[63] Continuation-in-part of application No. 08/816,930, Mar. 13, 1997, Pat. No. 5,910,604, and application No. 08/712,536, Sep. 11, 1996, abandoned.

[30] Foreign Application Priority Data

Sep. 13, 1995 [GB] United Kingdom ............ 9518704

[51] Int. Cl.$^7$ .............................................. C07C 205/00
[52] U.S. Cl. ......................................................... 562/435
[58] Field of Search .............................................. 562/435

[56] References Cited

U.S. PATENT DOCUMENTS 5,446,197   8/1995   Sandison .................... 562/435

*Primary Examiner*—Robert Gerstl
*Attorney, Agent, or Firm*—Dianne Burkhard

[57] ABSTRACT

A process for the purification of a compound of general formula I:

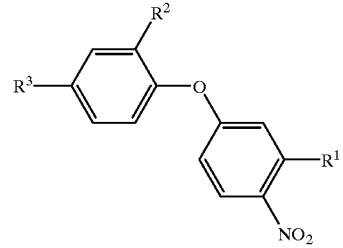

wherein $R^1$ is hydrogen or $C_1$–$C_6$ alkyl, $C_2$–$C_6$ alkenyl or $C_2$–$C_6$ alkynyl, any of which may optionally be substituted with one or more substituents selected from halogen and hydroxy; or $COOR^4$, $COR^6$, $CONR^4R^5$ or $CONHSO_2R^4$; $R^4$ and $R^5$ independently represent hydrogen or $C_1$–$C_4$ alkyl optionally substituted with one or more halogen atoms; $R^6$ is a halogen atom or a group $R^4$; $R^2$ is hydrogen or halo; and $R^3$ is $C_1$–$C_4$ alkyl, $C_2$–$C_4$ alkenyl or $C_2$–$C_4$ alkynyl, any of which may optionally be substituted with one or more halogen atoms; or halo;

or, where appropriate, a salt thereof;

from a mixture containing the compound of general formula I together with one or more isomers or di-nitrated analogues thereof; the process comprising dissolving the mixture in a suitable crystallisation solvent and recrystallising the product from the resulting crystallisation solution wherein the crystallisation solution contains not more than 25% loading of the compound of general formula I, loading being defined as:

$$\frac{\text{weight of pure compound of formula I} \times 100}{\text{weight of pure compound of formula I} + \text{weight of solvent}}$$

and wherein the temperature to which the solution is cooled for crystallisation is not greater than about 30° C.; wherein, after the addition of the crystallising solvent but before recrystallisation, the crystallisation solution is subjected to at least one wash with an aqueous solution having an acid pH followed by back extraction with fresh crystallising solvent. The process is particularly useful for purifying acifluorfen produced via a route starting with m-cresol.

31 Claims, No Drawings

PURIFICATION PROCESS

CROSS-REFERENCE TO RELATED APPLICATIONS

This is a continuation-in-part of applications Ser. No. 08/712,536 filed Sep. 11, 1996, abandoned, and 08/816,930 filed Mar.13, 1997, now U.S. Pat. No. 5,910,604.

The present invention relates to a process for the purification of diphenyl ether compounds which are useful as herbicides or as intermediates in the synthesis of herbicides. In particular, it relates to a process for obtaining particular nitrated isomers of diphenyl ether compounds from mixtures containing other nitrated isomers.

Diphenyl ether herbicides are known, for example from EP-A-0022610 which relates to herbicides of the formula:

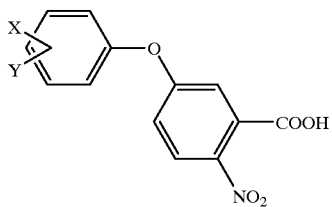

wherein X and Y may be H, F, Cl, Br, $CF_3$, $OCF_2CHZ_2$ (Z=Cl, Br, F), $OCH_3$, CN, $CO_2R$ (R=lower alkyl), $C_6H_5$, O-alkyl, $NO_2$ or $SO_2$-lower alkyl;

and also describes a process for making these compounds by nitrating a compound of the formula:

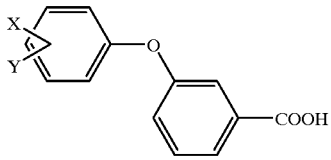

wherein X and Y are as defined above.

Suggested nitrating agents for this reaction include mixtures of nitric and sulfuric acids and the recommended reaction solvent is dichloromethane. The nitration process is said to give a yield of 75.4% but no details are given of the purity of the product or the presence of other nitrated isomers.

U.S. Pat. No. 4,031,131 describes similar compounds to the above which are prepared in a similar manner. Suggested nitrating agents include potassium nitrate or mixed nitric and sulphuric acids and the reaction is carried out in dichloromethane. An extremely high yield (>95%) is claimed for the nitration reaction but, again, there are no details given about the purity of the product. Nitration reactions using mixed nitric and sulfuric acids may also be carried out in the presence of acetic anhydride.

EP-A-0003416 and EP-A-0274194 both relate to the synthesis of herbicidal compounds of the formula:

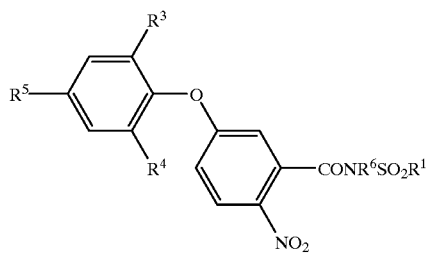

wherein $R^1$ is alkyl optionally substituted with fluorine or optionally substituted phenyl;

$R^3$ is H, F, Cl, Br, I, alkyl, trifluoromethyl or CN;

$R^4$ is H, F, Cl, Br, I or trifluoromethyl;

$R^5$ is F, Cl, Br, I or trifluoromethyl; and $R^6$ is H or $C_1$–$C_4$ alkyl.

In EP-A-0003416, these compounds may be obtained by nitrating the corresponding carboxylic acid or carboxamide and then converting to the sulfonamide or by nitrating the sulfonamide itself. A nitration reaction is described in Example 7 where the solvent is 1,2-dichloroethane and the nitrating agent is a mixture of potassium nitrate and concentrated sulfuric acid.

EP-A-0274194 relates, in particular, to a process for the nitration of compounds of the formula:

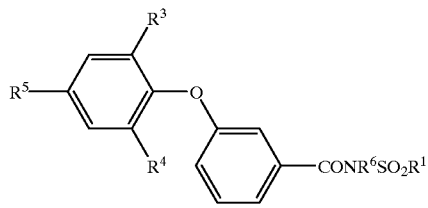

The nitration reaction is said to be carried out using a conventional nitrating agent such as concentrated nitric acid or sodium nitrate or mixtures of these with sulfuric acid. The reaction solvent is one which is resistant to nitration and examples of such solvents are said to include halogenated solvents such as dichloromethane, dichloroethane, dichloropropane, chlorofluorocarbons and aromatic solvents such as nitrobenzene.

However, none of these methods are particularly satisfactory for use on an industrial scale because they all have the common problem that the reaction yields a mixture of the required product and other nitrated isomers. Nitrated isomers of diphenyl ether compounds are often extremely difficult to separate from one another and the quantity of other isomers is often too high for the final product to fulfil the requirements of the regulatory authorities for herbicides. The problem tends to be further exacerbated if the nitrated product is an intermediate in the synthesis of a herbicide rather than the required herbicide itself because the mixture of nitrated compounds means that larger quantities of other reagents must be used than would be necessary if the nitrated isomers could be separated satisfactorily. It is therefore important to ensure that the nitration process produces a product mixture containing the highest possible proportion of the desired isomer.

The problem of obtaining mixtures of isomers from the nitration process was recognised by the authors of GB-A-2103214 who describe a process in which a compound of the formula:

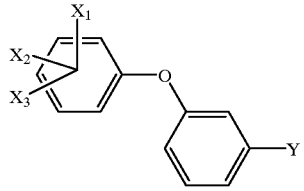

wherein each of $X_1$, $X_2$ and $X_3$, is H, F, Cl, Br, $CF_3$, $OCF_3$, $CHZ_2$ (where Z is F, Cl or Br), $OCF_3$, CN, COOR (R is lower alkyl), phenyl, lower alkoxy or $NO_2R$ and at least one of $X_1$, $X_2$ and $X_3$ is other than hydrogen; and Y is COOR or carboxy;
is nitrated to give a product of the formula:

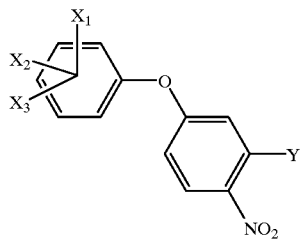

wherein $X_1$, $X_2$, $X_3$ and Y are as defined above. The document relates especially to acifluorfen, the compound in which $X_1$ is 2-chloro, $X_2$ is 4-trifluoromethyl, $X_3$ is hydrogen and Y is COOH.

According to this prior art document, the product is purified by selectively dissolving unwanted isomers and other by-products in a suitable solvent. Examples of solvents which are said to be suitable for this purpose include hydrocarbons such as pentane, hexane, heptane, cyclopentane, cyclohexane, cycloheptane, benzene, toluene, xylenes and mixtures of xylenes, ethylbenzene, cumene, pseudo-cumene, ethyl-toluene and trimethylbenzene. Alternatively, it is suggested that chlorohydrocarbons may be used and examples given are 1,2-dichloroethane, methylene chloride, chloroform and chlorobenzene. Xylenes appear to be especially preferred and suggested amounts are about 0.35 to 0.45 moles of xylenes per mole of crude acifluorfen. The crude nitration product is dissolved in the chosen solvent at elevated temperature and maintained at this temperature for a considerable period of time. On cooling, acifluorfen crystallises out and is collected by centrifugation. The product obtained by the authors of GB-A-2103214 is said to be 82% pure.

However, the present inventors have found that the process described in GB-A-2103214, although partially effective, does not appear to give material of this degree of purity. In any case, it is desirable to be able to obtain material of an even greater degree of purity than specified in the prior art, particularly if additional process steps are required in order to obtain the required herbicidal compound.

Therefore in a first aspect of the invention there is provided a process for the purification of a compound of general formula I:

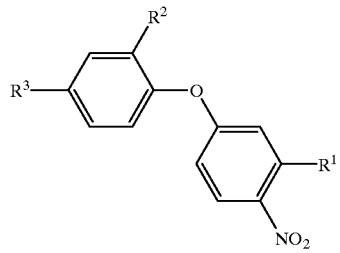

wherein $R^1$ is hydrogen or $C_1$–$C_6$ alkyl, $C_2$–$C_6$ alkenyl or $C_2$–$C_6$ alkynyl, any of which may optionally be substituted with one or more substituents selected from halogen and hydroxy; or $COOR^4$, $COR^6$, $CONR^4R^5$ or $CONHSO_2R^4$;

$R^4$ and $R^5$ independently represent hydrogen or $C_1$–$C_4$ alkyl optionally substituted with one or more halogen atoms;

$R^6$ is a halogen atom or a group $R^4$;

$R^2$ is hydrogen or halo; and $R^3$ is $C_1$–$C_4$ alkyl, $C_2$–$C_4$ alkenyl or $C_2$–$C_4$ alkynyl, any of which may optionally be substituted with one or more halogen atoms; or halo;

or, where appropriate, a salt thereof;

from a mixture containing the compound of general formula I together with one or more isomers or di-nitrated analogues thereof; the process comprising dissolving the mixture in a suitable crystallising solvent and recrystallising the product from the resulting crystallisation solution wherein the crystallisation solution contains not more than 25% loading of the compound of general formula I and the temperature to which the solution is cooled for crystallisation is not greater than about 30° C.

In the present specification, loading is defined as:

$$\frac{\text{weight of pure compound of formula I} \times 100}{\text{weight of pure compound of formula I} + \text{weight of solvent}}$$

In order to calculate the loading of the crystallisation solution, it is therefore essential to know the amount of isomer of general formula I present in the product mixture.

The present inventors have also found that significant improvements in the yield of pure compound are possible using the process of the present invention in which, after the addition of the crystallising solvent but before recrystallisation, the crystallisation solution is subjected to at least one wash with an aqueous solution having an acid pH.

Therefore in a second aspect of the invention there is provided a process for the purification of a compound of general formula I:

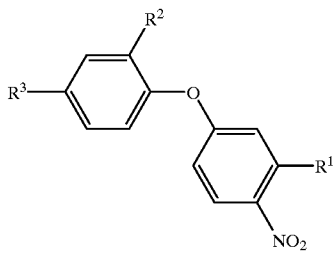

wherein $R^1$ is hydrogen or $C_1$–$C_6$ alkyl, $C_2$–$C_6$ alkenyl or $C_2$–$C_6$ alkynyl, any of which may optionally be substituted with one or more substituents selected from halogen and hydroxy; or $COOR^4$, $COR^6$, $CONR^4R^5$ or $CONHSO_2R^4$;

$R^4$ and $R^5$ independently represent hydrogen or $C_1$–$C_4$ alkyl optionally substituted with one or more halogen atoms;

$R^6$ is a halogen atom or a group $R^4$;

$R^2$ is hydrogen or halo; and $R^3$ is $C_1$–$C_4$ alkyl, $C_2$–$C_4$ alkenyl or $C_2$–$C_4$ alkynyl, any of which may optionally be substituted with one or more halogen atoms; or halo;

or, where appropriate, a salt thereof;

from a mixture containing the compound of general formula I together with one or more isomers or di-nitrated analogues thereof; the process comprising dissolving the mixture in a suitable crystallising solvent and recrystallising the product from the resulting crystallisation solution wherein the crystallisation solution contains not more than 25% loading of the compound of general formula I and the temperature to which the solution is cooled for crystallisation is not greater than about 30° C.; wherein, after the addition of the crystallising solvent but before recrystallisation, the crystallisation solution is subjected to at least one wash with an aqueous solution having an acid pH.

When the process of the present invention involves washing the crystallisation solution with an aqueous solution having an acid pH, the yield of pure compound of general formula I increases as the number of washes increases. Therefore it is often desirable to wash the crystallisation solution up to, for example, five times, e.g. twice or three times.

All washes comprise preferably 0.2 to 2.0 times the volume of the organic phase, and more preferably about 0.5 times the volume of the organic phase.

The washes are preferably conducted at a temperature of from 50 to 90° C., e.g. at about 80° C.

It has also been found that the pH range of the washing liquid appears to be of significance to the yield of the compound of general formula I which can be obtained. The aqueous solution used for washing the crystallisation solution preferably has a pH of 4.5 or less.

In a preferred embodiment of the invention the crystallisation solution is washed with an aqueous solution having a pH of from 3 to 3.8, more preferably an aqueous solution have ing a pH of from 3.3 to 3.5.

If the wash pH is greater than 3.8, the final yield may be reduced. This may be because above pH 3.8, there is salt formation in aqueous solution and the presence of salts in the product solution tends to inhibit the crystallisation of the free acid. If the pH of the washing solution is lower than 3, there may be no significant improvement in the the yield of the purified compound obtained. This may be due to the presence in the crude solution containing the compound of general formula I of the impurity of formula (4) which can be removed by the washing procedure described. The efficiency of removal of this impurity increases as the pH of the wash increases.

In a further preferred embodiment of the invention the crystallisation solution is washed with an aqueous solution having a pH of between 3.0 and 4.5, e.g. pH 3.5 to 4.5, followed by an additional wash at a pH of <2.0, e.g. pH 1.

In this embodiment use of an aqueous solution having a higher pH avoids the difficulty of controlling the pH at precisely 3 to 3.8, and the use of the final wash at pH <2.0 removes the adverse effect of the higher pH and converts any salt which is formed back to the free acid.

In a further preferred embodiment the process of the invention includes a first wash at pH <2.0, e.g. pH 1, followed by one to three washes at a pH of 3.0 to 4.5, followed by a final wash at pH <2.0, e.g. pH 1.

Washes having a pH of <2.0 my be prepared using a mineral acid, e.g hydrochloric, sulfuric or phosphoric acid, to obtain the desired pH. Washes having a pH of 3.0 to 4.5 may be prepared by adding an alkali, e.g an alkali metal hydroxide or carbonate, or a buffer, for example a salt of an acid having a pKa in the range 2–5, e.g formate/formic acid, to give the desired pH.

Because the pH controlled washes also take out some compound of formula I as well as impurities, doing more than one wash leads to an increased loss of compound of formula I but this is more than compensated for by the benefit of impurity removal.

Surprisingly however, it has been found that if the aqueous layers resulting from the pH controlled washes are adjusted to a suitable pH and then back extracted with fresh solvent, most (90–95%) of the compound of formula I can be recovered without re-extracting the impurities (<5%).

Therefore in a third aspect of the invention there is provided a process for the purification of a compound of general formula I:

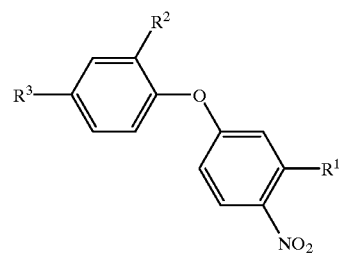

wherein $R^1$ is hydrogen or $C_1$–$C_6$ alkyl, $C_2$–$C_6$ alkenyl or $C_2$–$C_6$ alkynyl, any of which may optionally be substituted with one or more substituents selected from halogen and hydroxy; or $COOR^4$, $COR^6$, $CONR^4R^5$ or $CONHSO_2R^4$;

$R^4$ and $R^5$ independently represent hydrogen or $C_1$–$C_4$ alkyl optionally substituted with one or more halogen atoms;

$R^6$ is a halogen atom or a group $R^4$;

$R^2$ is hydrogen or halo; and $R^3$ is $C_1$–$C_4$ alkyl, $C_2$–$C_4$ alkenyl or $C_2$–$C_4$ alkynyl, any of which may optionally be substituted with one or more halogen atoms; or halo;

or, where appropriate, a salt thereof;

from a mixture containing the compound of general formula I together with one or more isomers or di-nitrated analogues thereof, the process comprising dissolving the mixture in a suitable crystallising solvent and recrystallising the product from the resulting crystallisation solution wherein the crystallisation solution contains not more than 25% loading of the compound of general formula I and the temperature to which the solution is cooled for crystallisation is not greater than about 30° C.; wherein, after the addition of the crystallising solvent but before recrystallisation, the crystallisation solution is subjected to at least one wash with an aqueous solution having an acid pH and the aqueous wash is back extracted with fresh crystallising solvent.

The resulting extracts are preferably recycled into the crystallisation process.

If multiple pH controlled washes are carried out, the washes are preferably combined prior to back-extraction.

The volume of solvent used for back extraction is not critical but generally the process uses preferably 0.2–3 times the volume of the aqueous phase, and preferably about 0.5–1 times the volume of the aqueous phase.

The back extraction is preferably conducted at a temperature of from 50 to 90° C., e.g. at about 80° C. and may be performed at pH 3.2–4.2 preferably at pH 3.5–3.8.

In a preferred embodiment of the invention the process includes the use of multiple, preferably two to three, pH controlled washes followed by back extraction of the combined washings. Additional yield gains are of the order of 3–4% may be obtained by this embodiment.

That back extraction is so beneficial is most surprising since the skilled person would not have been expected it to be so selective since the original pH controlled washing of the compound of formula I with crystallising solvent was so selective, in the opposite direction (i.e. for impurities not for compound of formula I).

Using the process of the present invention, it is possible to obtain a product of greater than 90% purity. This is a significant advantage when the product is a herbicide as regulatory authorities usually demand an active ingredient of a very high level of purity with minimal impurities. The advantage may be even greater when the product produced is an intermediate and additional steps must be carried out as reagents are not wasted in reacting with unwanted by-products.

The process of the present invention differs significantly from the process described in GB-A-2103214. Firstly, the authors of that document stated that, for xylenes, the optimum amount of product loading is from 0.35 to 0.45 moles of xylene per mole of acifluorfen. This is a solution containing at least 88% w/w of acifluorfen whereas, in the present invention, the crystallisation solution contains not more than 25% loading of acifluorfen. In a typical crude mixture containing about 70% acifluorfen, this corresponds to a crystallisation solution containing about 32% w/w of the crude mixture. Secondly, the crystallisation solution in this prior art document is not washed before the recrystallisation takes place.

U.S. Pat. No. 5446197 relates to a process which is similar to the process of the present invention. However, significantly, there is no step of washing the crystallisation solution at acid pH and the best yield of high purity compound of formula I achieved was 72% when using o-xylene as solvent.

In the context of the present invention, the term "$C_1$–$C_6$ alkyl" refers to a saturated straight or branched hydrocarbon chain containing from 1 to 6 carbon atoms. Examples include methyl, ethyl, n-propyl, t-butyl, n-pentyl and n-hexyl. The term "$C_1$–$C_4$ alkyl" is a subset of $C_1$–$C_6$ alkyl and refers to an alkyl group having up to 4 carbon atoms.

The term "$C_2$–$C_6$ alkenyl" refers to a straight or branched hydrocarbon chain containing from 2 to 6 carbon atoms and having at least one double bond. Examples include ethenyl, allyl, propenyl and hexenyl. The term "$C_2$–$C_4$ alkenyl" is a subset of $C_2$–$C_6$ alkenyl and refers to an alkenyl group having up to 4 carbon atoms.

The term "$C_2$–$C_6$ alkynyl" refers to a straight or branched hydrocarbon chain containing from 2 to 6 carbon atoms and having at least one triple bond. Examples include ethynyl, propynyl and hexynyl. The term "$C_2$–$C_4$ alkynyl" is a subset of $C_2$–$C_6$ alkynyl and refers to an alkynyl group having up to 4 carbon atoms.

The term "halogen" refers to fluorine, chlorine, bromine or iodine and the corresponding term "halo" refers to fluoro, chloro, bromo or iodo.

Although the process of the invention may be used for the purification of any compound of general formula I, it is especially preferred that $R^2$ is chloro and $R^3$ is trifluoromethyl. Particularly preferred compounds of general formula I are those in which $R^1$ is COOH or $CONHSO_2CH_3$. These compounds are 5-(2-chloro-α,α,α-trifluoro-4-tolyloxy)-2'-nitrobenzoic acid (acifluorfen) and 5-(2-chloro-α,α,α-trifluoro-4-tolyloxy)-N-methanesulfonyl-2'-nitrobenzamide (fomesafen), both of which are potent herbicidal compounds.

In the context of the present invention, compounds of general formula I are designated 4'-nitro isomers.

Other components of the product mixture which may be present include the 2'-nitro isomer of general formula:

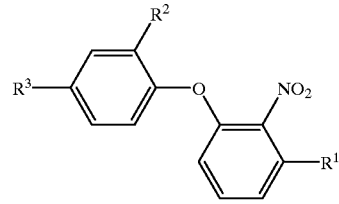

the 6'-nitro isomer:

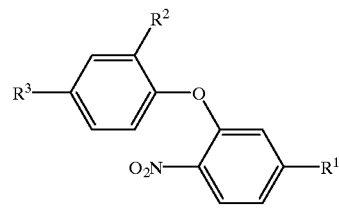

and the dinitro isomers (1) and (2):

(1)

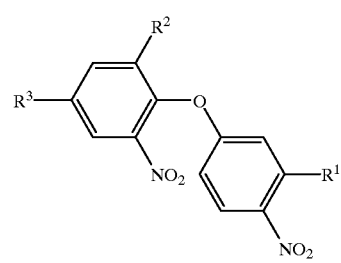

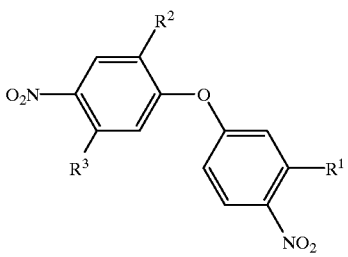

(2)

Further unwanted by-products include compound (3) which is formed by nitration of an isomer present as an impurity in the reactant:

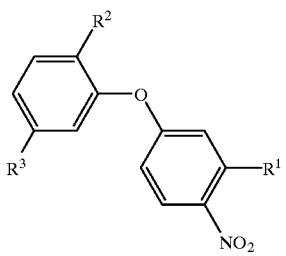

(3)

and compound (4):

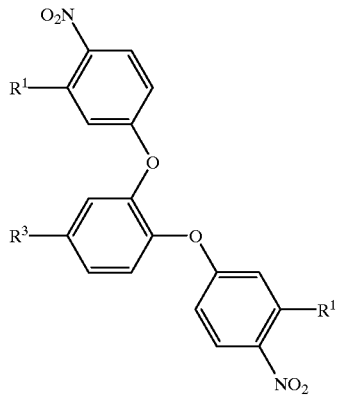

(4)

It is particularly important that purification of the desired product of general formula I should remove all, or substantially all, of the 2'-nitro isomer since this is the most difficult isomer to separate from the product by other methods. In addition, if the compound of general formula I is to be used as starting material in a further reaction, other nitrated isomers are also likely to react and this causes wastage of reagents. Again, the 2'-nitro isomer is a particularly important impurity as many of its reaction products are also difficult to separate from the reaction products of compounds of general formula I.

Impurities of formula (4) tend to be present when the compound of general formula I has been produced via a route starting from an alkylphenol (for example m-cresol when the compound of general formula I is acifluorfen or fomesafen). For this reason, although this route uses less expensive starting materials and should be more economic to operate, it has often been avoided in the past and the compound of general formula I produced instead via a route starting from 3-hydroxybenzoic acid. Indeed, this is the route recommended by the authors of both U.S. Pat. No. 5,446,197 and GB-A-2103214. The impure mixture containing the compound of general formula I used in the testing of the present invention was produced via the route starting from a 3-alkyl phenol and contains the impurity of formula (4). The presence of this impurity may be the reason why the purification methods of U.S. Pat. No. 5,446,197 and GB-A-2103214 appear to give inferior results in our hands.

Since it is economically preferable to prepare compounds of general formula I such as acifluorfen and fomesafen from a 3-alkyl phenol rather than from a benzoic acid, the process of the present invention has been developed with the intention of obtaining material of a high purity from that route. It does not appear to be possible to achieve this using prior art methods.

Only a narrow range of solvents is suitable for use in the present invention with examples being aromatic hydrocarbons, such as xylenes or mixtures of xylenes, and haloaromatics such as o-chlorotoluene, p-chlorotoluene, benzotrifluoride, 3,4-dichlorobenzotrifluoride, chlorobenzene, o-dichlorobenzene, m-dichlorobenzene, fluorobenzene, bromobenzene, and 2-fluorotoluene. Mixtures of any of the above solvents may also be suitable and also mixtures containing aromatic hydrocarbons with a co-solvent which may be one of the solvents mentioned above but may, alternatively be chosen from a much wider range of solvents including aliphatic hydrocarbons, esters, ethers, nitrites and halohydrocarbons.

Xylenes have been found to be particularly suitable solvents for use in the present invention with o-xylene giving better results than other xylenes or mixtures of xylenes.

The optimum loading of the crystallisation varies considerably according to the solvent which is chosen but is, in any case, not greater than about 25%. More typically, optimum loading is from 8% to 20%. For many solvents, for example xylenes, the loading may be, for example, from about 15 to 20% but with a few solvents it is necessary to reduce the loading even further with a product mixture loading of about 8 to 10% being used.

Although the temperature to which the solution is cooled to effect crystallisation may be as high as 30° C., the purity of the product may be increased considerably by reducing the temperature somewhat. It is greatly preferred, therefore that the temperature to which the solution is cooled to achieve crystallisation is not above 20° C., preferably about 0° to 15° C. with 0° to 5° being an optimal range. This is in contrast to the process described in GB-A-2103214 in which the crystallisation temperature recommended for optimum results is about 25° C.

A further factor which has been found to affect the purity of the product is the length of time for which the mixture is allowed to stand after crystallisation before recovery of the product. It has been found that many 2'-nitro isomers of general formula I are metastable in solution and tend to crystallise slowly, contaminating the desired product and reducing its purity after crystallisation. Therefore, it is preferred that the product slurry, after achieving crystallisation temperature, is not held for more than about four hours, more usually from about 1 to 2 hours, before physical separation of the product from the mother liquors.

Crystallisation may be achieved by any suitable method such as seeding the crystallisation solution with crystals of a pure compound of general formula I. It may be advantageous to carry out the seeding in several stages starting when the crystallisation solution is still hot and adding further crystals as it cools. In some circumstances, seeding of the crystallisation solution may not be necessary and cooling of the solution will cause rystallisation of the product.

The product may be separated from the slurry after crystallisation by any appropriate method but filtration is very often the most convenient way of doing this.

The mixture to be purified may be the crude product of a process for the nitration of a compound of general formula II:

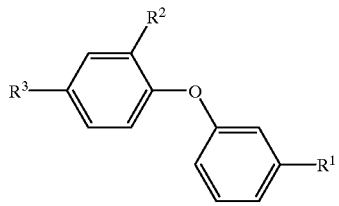

wherein $R^1$, $R^2$ and $R^3$ are as defined for general formula I.

Any conventional nitration method may be used, for example the nitration method disclosed in GB-A-2103214.

In one suitable method, the nitration agent may be nitric acid or a mixture of nitric and sulphuric acids although other types of nitrating agent may also be used. The reaction may take place in an organic solvent and suitable solvents include halogenated solvents such as dichloromethane (DCM), ethylene dichloride (EDC), chloroform, tetrachloroethylene (perklone) and dichlorobenzotrifluoride (DCBTF). Alternatively, solvents such as acetic acid, acetic anhydride, acetonitrile, ethers such as tetrahydrofuran (THF) or dioxane, sulpholane, nitrobenzene, nitromethane, liquid sulphur dioxide or liquid carbon dioxide. It is also advantageous to conduct the reaction in the presence of acetic anhydride and, in this case, it is preferred that the molar ratio of acetic anhydride to compound of general formula II is from about 1:1 to 3:1. The reaction temperature may be from about −15° to 15° C., more usually from about −10° to 10° C.

After the nitration reaction, the crude product must be removed from the reaction solvent and taken up in the crystallisation solvent. This may be achieved by washing with water to remove any acetic anhydride, acetic acid or mineral acid and then stripping off the reaction solvent completely, melting the product mixture and then taking up the melt in the crystallisation solvent. Alternatively, the product can be extracted from the nitration solvent as a salt (for example the sodium salt) into water and the solvent separated off for recycling. The salt solution may then be acidified in the presence of the hot recrystallisation solvent in order to extract the product for recrystallisation. When acidifying the salt solution, it has been found that adjusting the pH to 1 or less produces the most favourable results. Indeed, it seems that there may be an increase in yield of about 10% when the salt solution is at pH 1 compared with an identical process in which the salt solution is at pH 3. This process in which the impure product is not isolated and in which the pure product is obtained directly from an aqueous solution of the salt is especially useful as it simplifies the work up process after the nitration reaction. It is certainly a considerable improvement on the process described in U.S. Pat. No. 5,446,197 in which it is necessary to isolate a crude wet paste containing the compound to be purified.

When the nitration process is combined with either of these work-ups and the recrystallisation process of the first aspect of the invention, it is possible to obtain a product of over 90% purity in a yield of greater than 70%.

The step of taking up the crude product in the crystallisation solvent may be preceded by an initial partial purification step which itself forms a further aspect of the present invention.

In this aspect of the invention, there is provided a process for partial purification of a product mixture obtained from the nitration of a compound of general formula II to give a compound of general formula I, the process comprising removing the reaction solvent and treating the resultant crude product with a mixture of water and a water-miscible polar solvent.

In one method of achieving partial purification, any acetic anhydride may be hydrolysed with water to give acetic acid and this, or acetic acid from any other source, may be left in the reaction mass to act as the polar solvent. The reaction solvent may then be removed by distillation or steam distillation leaving a molten crude product containing some acetic acid which may then be treated with additional quantities of acetic acid and water to facilitate partial purification without substantial dissolution of the required isomer.

Alternatively, the crude product of the nitration reaction, after washing and removal of the reaction solvent, may be treated with a mixture of a polar solvent and water to achieve partial dissolution of impurities and isomers without substantial loss of the desired product which can then be recovered by filtration. In this case, suitable polar solvents include solvents such as formic acid, acetic acid, propionic acid, methanol, acetonitrile and acetone.

The proportion of polar solvent to water may be in the range of from about 3:7 to 7:3, more particularly from about 2:3 to 3:2, and the amount of crude nitrated isomer mixture in the polar solvent/water solution may be from about 10 to 80% by weight, preferably about 15 to 30% by weight. The initial purification step may be carried out at a temperature of from about 10° to 60° C., more usually from about 15° to 30° C.

An initial purification process such as those described above leads to an improvement in the quality of the crude nitration product from about 70% strength (i.e. 70% by weight of the desired isomer of general formula I) to about 80% strength. A nitration process followed by the initial purification step and the recrystallisation process of the first aspect of the invention is high yielding with a recovery of the desired isomer of greater than 90% and often greater than 95%. The initial purification step of the second aspect of the invention is particularly effective for the removal of products of over nitration and also other impurities which commonly occur in a product derived from a multi-step synthesis. The product from the initial purification process has improved characteristics for purification by recrystallisation.

In addition to being a herbicide in its own right, acifluorfen may also serve as an intermediate in the synthesis of fomesafen. The acifluorfen may be converted to its acid chloride which may then be reacted with methane sulphonamide to give fomesafen. Both of these steps may be carried out by conventional methods, for example as set out in EP-A-0003416. It is a particular advantage when using this method to start out with pure acifluorfen as the reaction with methane sulphonamide is an expensive process and it is highly desirable not to waste reagents by sulphonamidating unwanted nitro-isomers to produce unwanted isomers of fomesafen.

The present invention therefore provides a route for the synthesis of pure acifluorfen and its subsequent conversion to pure fomesafen.

As already mentioned, one of the particular advantages of the purification process of the present invention is that it can be used to purify acifluorfen produced from m-cresol and 3,4-dichlorobenzyltrifluoride (DCBTF). As discussed above, m-cresol is less expensive than 3-hydroxybenzoic acid, which is an alternative starting material, but the route starting from m-cresol tends to yield acifluorfen of insufficient purity for use as a herbicide or as an intermediate to other compounds such as fomesafen. However, using the purification process of the present invention, it has proved possible to purify acifluorfen produced by the m-cresol route.

Therefore, in a further aspect of the present invention, there is provided a process for the preparation of 5-(2-chloro-α,α,α-trifluoro-4-tolyloxy)-2'-nitrobenzoic acid (acifluorfen), the process comprising the steps of:

a) reacting m-cresol with DCBTF to produce 3-(2-chloro-α,α,α-trifluoro-4-tolyloxy)toluene;

b) oxidising 3-(2-chloro-α,α,α-trifluoro-4-tolyloxy) toluene to give 3-(2-chloro-α,α,α-trifluoro-4-tolyloxy) benzoic acid;

c) nitrating 3-(2-chloro-α,α,α-trifluoro-4-tolyloxy) benzoic acid to give acifluorfen; and d) purifying the acifluorfen by a method according to the methods described above.

The invention will now be further illustrated with reference to the following examples.

EXAMPLE 1
General Procedure for Recrystallisation of Solid Acifluorfen

Solid crude acifluorfen was added to the recrystallisation solvent and heated to about 80° C. to dissolve. Any water was separated off and remaining traces of water were removed by azeotropic distillation. The solution was cooled to about 60° C. and a seed of pure acifluorfen was added and further seeds added at 5° C. intervals as the solution was cooled until crystallisation occurred. Cooling was continued to the required temperature and the product was isolated by filtration and washed with a little fresh solvent.

The crude acifluorfen had the following composition:
acifluorfen 69–75%
2'-nitro 7–9%
6'-nitro 3.5–4.5%
Isomer (3) 4.5–5%
Dinitros 0.5–2%

EXAMPLE 2

General Procedure for Extraction of Acifluorfen from its Sodium Salt and Recrystallisation Acifluorfen sodium salt solution at 10–40% concentration (as free acid) was mixed with the recrystallisation solvent and heated to 80° C. Mineral acid was added to adjust the pH of the solution to 3–3.5 and the two layers were allowed to separate. The aqueous layer was separated and the organic layer was washed with one third volume water at 70–80° C. The aqueous layer was removed and the solution dried by azeotropic removal of water. The solution was cooled to effect crystallisation and the product recovered by filtration.

Tables I and II give the results for the purification procedure described in Example 1 and Tables III and IV give results for the purification process described in Example 2. In each case, a variety of different solvents, loadings of the crystallisation solution, filtration temperatures and stir times were used. In Tables I to IV, the following abbreviations are used:

| | |
|---|---|
| Exp | Experiment No.; |
| Stg. Mtl. Str. | Starting material strength (i.e. % required product in mixture); |
| Wt Solv. g | Weight of crystallisation solvent in grams; |
| TEA | triethylamine; |
| AcOH | acetic acid; |
| MCB | monochlorobenzene; |
| MDCB | m-dichlorobenzene; |
| ODCB | o-dichlorobenzene |
| tech xylene | mixture of xylenes; |
| Tol | toluene; |
| cyclohex | cyclohexane. |

TABLE I

| | Stg. | | Filt. | | | | Product Analysis % w/w | | | | |
|---|---|---|---|---|---|---|---|---|---|---|---|
| Exp. | Mtl. Str % | Solvent | Loading % | Temp. ° C. | Stir Time hr | Recovery % | Total dinitro | Isomer(3) % | Product % | 2'-nitro % | 6'-nitro % |
| 1 | 71.7 | 2-Chlorotoluene | 14.99 | 30 | 0.00 | 59.33 | 0.8 | 0.8 | 95.6 | 0 | 0 |
| 2 | 71.7 | 2-Chlorotoluene | 20.00 | 30 | 0.00 | 62.98 | 0.5 | 0.6 | 91.3 | 3.7 | 0.1 |
| 3 | 71.7 | 2-Chlorotoluene | 19.05 | 30 | 0.00 | 69.89 | 0.8 | 0.6 | 90.2 | 5.9 | 0 |
| 4 | 72.2 | 2-Chlorotoluene | 15.00 | 30 | 0.00 | 60.05 | 0.7 | 1 | 93.8 | 0.6 | 0 |
| 5 | 72.2 | 2-Chlorotoluene | 15.00 | 30 | 0.00 | 47.23 | 0.5 | 1.2 | 90.8 | 1 | 0 |
| 6 | 72.2 | 2-Chlorotoluene | 20.11 | 30 | 0.00 | 65.33 | 0.7 | 1 | 78.8 | 8.2 | 0 |
| 7 | 75.4 | 2-Chlorotoluene | 6.48 | 15 | 0.50 | 54.83 | 0.52 | 0.5 | 93.9 | 0.4 | 0 |
| 8 | 79.7 | 2-Chlorotoluene | 11.59 | 15 | 0.50 | 74.08 | 0.5 | 0.3 | 91.6 | 6.3 | 0.1 |
| 9 | 85.5 | 2-Chlorotoluene | 15.00 | 30 | 0.00 | 74.83 | 0.2 | 0.2 | 90.7 | 7.8 | 0 |
| 10 | 69.3 | 2-Chlorotoluene/TEA | 19.86 | 30 | 0.00 | 52.97 | 0.6 | 0.5 | 93.9 | 0.9 | 0 |
| 11 | 71.2 | 2-Fluorotoluene | 15.04 | 15 | 1 | 63.63 | 0.5 | 0.8 | 81.6 | 5.2 | 0.1 |
| 12 | 77.16 | 4-Chlorotoluene | 9.98 | 15 | 1.00 | 76.21 | 0.2 | 0.25 | 92 | 7.5 | 0 |
| 13 | 67.9 | AcOH/water 40/60 | 21.50 | 55 | 1.00 | 96.59 | 1.73 | 6.2 | 72 | 10 | 5 |
| 14 | 67.9 | AcOH/water 40/60 | 21.50 | 45 | 1.00 | 90.34 | 1.1 | 6.2 | 72.2 | 10.2 | 4.6 |
| 15 | 70.3 | AcOH/water 40/60 | 21.61 | 55 | 1.00 | 90.13 | 1.98 | 4.2 | 71.1 | 8.7 | 4.3 |
| 16 | 69.6 | AcOH/water 42/58 | 16.65 | 20 | 16.00 | 85.67 | 1.3 | 3.3 | 75.4 | 8.9 | 4.4 |
| 17 | 70.3 | AcOH/water 42/58 | 21.60 | 55/45 | 1.00 | 92.33 | 1.45 | 3.7 | 73.3 | 9 | 4.2 |
| 18 | 70.3 | AcOH/water 42/58 | 21.61 | 55 | 1.00 | 91.46 | 1.5 | 3.5 | 74.3 | 9.1 | 3.7 |
| 19 | 69.5 | AcOH/water 45/55 | 16.09 | 20 | 16.00 | 87.25 | 0.9 | 2 | 79.7 | 10.1 | 4.5 |
| 20 | 69.5 | AcOH/water 45/55 | 19.77 | 20 | 16.00 | 85.82 | 1.2 | 2.2 | 76.5 | 10.1 | 4.7 |
| 21 | 71.7 | AcOH/water 45/55 | 19.48 | 20 | 0.50 | 74.72 | 0.5 | 1.4 | 80.7 | 9.8 | 0.8 |
| 22 | 68.9 | AcOH/water 50/50 | 40.68 | 22 | 2 | 96.41 | 0.43 | 2.25 | 79.2 | 10 | 4.4 |
| 23 | 68.9 | AcOH/water 50/50 | 31.58 | 22 | 2 | 86.22 | 0.38 | 2.25 | 78.8 | 10.2 | 4.45 |

TABLE I-continued

| Exp. | Stg. Mtl. Str % | Solvent | Loading % | Filt. Temp. °C | Stir Time hr | Recovery % | Product Analysis % w/w ||||| 
|---|---|---|---|---|---|---|---|---|---|---|---|
| | | | | | | | Total dinitro | Isomer(3) % | Product % | 2'-nitro % | 6'-nitro % |
| 24 | 75.4 | Benzotrifluoride | 5.88 | 15 | 0.50 | 67.41 | 0.6 | 0.6 | 90.8 | 1.8 | 0 |
| 25 | 75.4 | Benzotrifluoride | 7.61 | 15 | 0.50 | 69.16 | 0.62 | 0.67 | 88 | 6.04 | 0 |
| 26 | 75.4 | Benzotrifluoride | 7.61 | 10 | 0.50 | 80.17 | 0.67 | 0.62 | 88.8 | 6.6 | 0 |
| 27 | 75.5 | Benzotrifluoride | 5.92 | 15 | 1.00 | 77.06 | 0.6 | 0.9 | 91.1 | 6.2 | 0.2 |
| 28 | 75.5 | Benzotrifluoride | 5.92 | 10 | 0.50 | 79.82 | 0.66 | 0.7 | 90.4 | 6.74 | 0.18 |
| 29 | 75.5 | Benzotrifluoride | 7.63 | 15 | 0.50 | 79.72 | 0.68 | 0.7 | 90.4 | 8.1 | 0.13 |
| 30 | 76.5 | Benzotrifluoride | 10.59 | 15 | 0.50 | 80.08 | 0.6 | 0.4 | 88.4 | 9.1 | 0 |
| 31 | 71.2 | Bromobenzene | 15.04 | 15 | 1 | 70.51 | 0.5 | 1.1 | 85.5 | 5.9 | 0.15 |
| 32 | 75.4 | MCB | 6.34 | 15 | 0.50 | 40.04 | 0.54 | 0.7 | 94.3 | 0 | 0 |
| 33 | 75.5 | MCB | 8.21 | 15 | 0.50 | 52.09 | 0.5 | 0.8 | 96.7 | 0 | 0 |
| 34 | 75.5 | MCB | 8.21 | 10 | 0.50 | 57.02 | 0.49 | 0.75 | 95.9 | 0.2 | 0 |
| 35 | 77.16 | MCB | 14.97 | 15 | 1 | 79.35 | 0.14 | 0.25 | 86.7 | 8.8 | 0 |
| 36 | 77.16 | MCB | 13.02 | 15 | 1 | 79.00 | 0.2 | 0.2 | 87.6 | 8.9 | 0 |
| 37 | 79.7 | MCB | 11.41 | 15 | 0.50 | 67.90 | 0.49 | 0.5 | 96.2 | 3.4 | 0 |
| 38 | 79.9 | MCB | 11.99 | 15 | 1 | 78.11 | 1.57 | 0.3 | 92.5 | 1.66 | 0.1 |
| 39 | 79.9 | MCB | 14.98 | 15 | 1 | 81.01 | 1.7 | 0.4 | 90.5 | 4.4 | 0.1 |
| 40 | 79.9 | MCB | 14.98 | 15 | 1 | 83.40 | 1.6 | 0.5 | 91.2 | 4.7 | 0.2 |
| 41 | 71.2 | MDCB | 15.04 | 15 | 1 | 77.39 | 0.6 | 0.8 | 86.5 | 7 | 0.2 |
| 42 | 71.2 | MDCB | 13.01 | | | 0.00 | 0.6 | 0.8 | 84.5 | 7.4 | 0.2 |
| 43 | 68.9 | o-xylene | 11.97 | 15 | 3.00 | 54.15 | 0.38 | 1.1 | 88 | 0.63 | 0.1 |
| 44 | 68.9 | o-xylene | 9.90 | 15 | 3.00 | 53.31 | 0.39 | 1 | 87.4 | 0.8 | 0.11 |
| 45 | 68.9 | o-xylene | 13.75 | 15 | 1.00 | 59.26 | 0.34 | 0.8 | 85.2 | 2.85 | 0.2 |
| 46 | 69 | o-xylene | 17.97 | 25 | 1 | 70.87 | 4.2 | 1 | 91.4 | 1.1 | 0.8 |
| 47 | 71.2 | o-xylene | 16.51 | 15 | 1.00 | 61.20 | 0.5 | 0.9 | 90.5 | 0.6 | 0.1 |
| 48 | 71.2 | o-xylene | 13.01 | 15 | 1.00 | 78.13 | 0.85 | 0.84 | 84.5 | 7.4 | 0.2 |
| 49 | 71.4 | o-xylene | 16.10 | 15 | 1.00 | 62.24 | 0.3 | 0.7 | 91.9 | 0 | 0 |
| 50 | 73.3 | o-xylene | 10.02 | 15 | 1.00 | 61.26 | 0.59 | 0.8 | 94.9 | 1.06 | 0.2 |
| 51 | 73.3 | o-xylene | 15.02 | 15 | 1.00 | 71.23 | 0.74 | 0.63 | 87.8 | 7.3 | 0.2 |
| 52 | 77.16 | o-xylene | 11.98 | 30 | 1 | 63.43 | 0.16 | 0.3 | 91.3 | 5.1 | 0.04 |
| 53 | 77.16 | o-xylene | 9.98 | 20 | 1 | 73.03 | 0.15 | 0.25 | 93.6 | 5.9 | 0 |
| 54 | 79.9 | o-xylene | 11.99 | 15 | 1 | 78.18 | 1.7 | 0.4 | 96 | 0.8 | 0.1 |
| 55 | 79.9 | o-xylene | 11.99 | 25 | 1 | 77.43 | 1.76 | 0.2 | 93.4 | 2.2 | 0.1 |
| 56 | 79.9 | o-xylene | 14.98 | 25 | 1 | 79.84 | 1.2 | 0.3 | 91.3 | 3.8 | 0.1 |
| 57 | 67.9 | ODCB | 9.82 | 15 | 1.00 | 62.78 | 0.54 | 2.3 | 93.1 | 0 | 0 |
| 58 | 67.9 | ODCB | 15.00 | 15 | 1.00 | 68.43 | 0.66 | 1.5 | 86.6 | 5.5 | 0 |
| 59 | 68.9 | ODCB | 9.90 | 15 | 1.00 | 67.00 | 0.35 | 1.1 | 90 | 0.35 | 0.1 |
| 60 | 68.9 | ODCB | 11.97 | 15 | 1.00 | 69.84 | 0.39 | 1.05 | 90.1 | 0.63 | 0.1 |
| 61 | 68.9 | ODCB | 9.90 | 15 | 1.00 | 64.40 | 0.41 | 1.3 | 89 | 0.66 | 0.2 |
| 62 | 68.9 | ODCB | 9.90 | 15 | 3.00 | 66.24 | 0.4 | 1.05 | 90.2 | 1.4 | 0.1 |
| 63 | 68.9 | ODCB | 11.96 | 15 | 1.00 | 69.42 | 0.3 | 1.2 | 89.3 | 2.2 | 0.3 |
| 64 | 68.9 | ODCB | 11.97 | 15 | 3.00 | 70.51 | 0.26 | 1 | 88 | 3.6 | 0.2 |
| 65 | 68.9 | ODCB | 13.80 | 15 | 1.00 | 70.13 | 0.25 | 0.8 | 84.8 | 5 | 0.2 |
| 66 | 69 | ODCB | 17.97 | 15 | 1 | 78.00 | 3.7 | 0.9 | 89.7 | 0.5 | 0 |
| 67 | 69.6 | ODCB | 9.81 | 15 | 0.50 | 42.94 | 0.72 | 0.94 | 92.8 | 0.t | 0 |
| 68 | 69.93 | ODCB | 20.45 | 30 | | 78.43 | 0.4 | 0.6 | 88.4 | 7.7 | 0 |
| 69 | 70 | ODCB | 14.86 | 15 | 1.00 | 58.16 | 0.77 | 0.9 | 95.9 | 0.2 | 0 |
| 70 | 70 | ODCB | 19.85 | 15 | 1.00 | 76.20 | 0.61 | i.1 | 88.8 | 7.3 | 0.3 |
| 71 | 72 | ODCB | 9.90 | 15 | 1.00 | 67.09 | 0.56 | 1.7 | 94.2 | 0.6 | 0.14 |
| 72 | 73.3 | ODCB | 9.83 | 15 | 1.00 | 68.58 | 0.81 | 0.6 | 93.2 | 0.3 | 0.1 |
| 73 | 73.3 | ODCB | 11.99 | 15 | 1.00 | 69.44 | 0.71 | 0.8 | 92.8 | 0.5 | 0.1 |
| 74 | 73.3 | ODCB | 13.80 | 15 | 1.00 | 73.58 | 1.1 | 0.6 | 92.2 | 3.13 | 0.16 |
| 75 | 75.5 | ODCB | 9.81 | 15 | 0.50 | 66.15 | 0.59 | 1 | 94.4 | 3.4 | 0 |
| 76 | 75.5 | ODCB | 12.04 | 15 | 1.00 | 73.69 | 0.57 | 1.06 | 89.3 | 6.2 | 0 |
| 77 | 76.5 | ODCB | 9.90 | 15 | 0.50 | 75.90 | 0.5 | 0.5 | 97.7 | 0.9 | 0 |
| 78 | 77.16 | ODCB | 7.96 | 15 | 1 | 69.83 | 0.2 | 0.4 | 95.2 | 0.1 | 0 |
| 79 | 77.16 | ODCB | 8.97 | 15 | 1 | 78.49 | 0.2 | 0.3 | 96.3 | 1.7 | 0 |
| 80 | 77.16 | ODCB | 14.97 | 25 | 1 | 81.37 | 0.2 | 0.45 | 90.9 | 5.4 | 0 |
| 81 | 77.16 | ODCB | 9.98 | 15 | 1 | 81.30 | 0.15 | 0.4 | 92.2 | 6.8 | 0 |
| 82 | 79.7 | ODCB | 9.91 | 15 | 1.00 | 75.75 | 0.5 | 0.4 | 97.5 | 0 | 0 |
| 83 | 80.7 | ODCB | 9.91 | 15 | 0.50 | 80.05 | 0.1 | 0.4 | 96.9 | 0.5 | 0 |
| 84 | 80.7 | ODCB | 12.47 | 15 | 0.50 | 86.39 | 0 | 0.3 | 90.7 | 7.2 | 0 |
| 85 | 69.3 | ODCB/TEA | 19.86 | 30 | 0.00 | 64.76 | 0.2 | 0.7 | 75.5 | 2.6 | 0 |
| 86 | 79.9 | p-xylene | 11.02 | 25 | 1 | 77.35 | 2.06 | 0.2 | 93.9 | 1.63 | 0.1 |
| 87 | 79.9 | p-xylene | 14.00 | 25 | 1 | 77.21 | 1.88 | 0.3 | 91.8 | 3.4 | 0.1 |
| 88 | 79.9 | p-xylene | 11.02 | 15 | 1 | 81.04 | 2 | 0.4 | 90.6 | 3.6 | 0 |
| 89 | 69.3 | Perklone/TEA | 14.77 | 30 | 0.00 | 60.59 | 0 | 3.3 | 72.4 | 8.3 | 0 |
| 90 | 70 | techxylene | 9.90 | 15 | 1.00 | 53.10 | 0.85 | 1 | 96.1 | 0.75 | 0.1 |
| 91 | 70 | techxylene | 15.86 | 15 | 1.00 | 74.67 | 0 | 0.8 | 88.3 | 9.4 | 0.3 |
| 92 | 77.16 | techxylene | 9.98 | 30 | 1 | 67.69 | 0.15 | 0.2 | 86.6 | 9.5 | 0 |
| 93 | 77.16 | techxylene | 11.98 | 30 | 1 | 80.59 | 0.2 | 0.3 | 88.7 | 9.9 | 0.1 |
| 94 | 79.2 | techxylene | 12.04 | 20 | 1 | 75.79 | 0.14 | 0.4 | 84.8 | 10.3 | 0.16 |
| 95 | 79.2 | techxylene | 12.04 | 30 | 1 | 44.83 | 0.14 | 0.3 | 85.4 | 10.7 | 0.17 |
| 96 | 69.93 | tech-xylene | 16.86 | 25 | 0.00 | 53.70 | 0.4 | 0.6 | 88.9 | 6.2 | 0 |
| 97 | 69.3 | Tol/cyclohex/TBA | 20.00 | 30 | 0.00 | 43.06 | 1 | 0.5 | 82.8 | 6.7 | 0 |

TABLE I-continued

| Exp. | Stg. Mtl. Str % | Solvent | Loading % | Filt. Temp. °C. | Stir Time hr | Recovery % | Total dinitro | Isomer(3) % | Product % | 2'-nitro % | 6'-nitro % |
|---|---|---|---|---|---|---|---|---|---|---|---|
| 98 | 69.93 | Toluene | 20.48 | 30 | 0.00 | 50.58 | 0.8 | 0.7 | 88.3 | 5.7 | 0 |
| 99 | 71.7 | Toluene | 20.00 | 25 | 1.00 | 43.06 | 0.5 | 0.5 | 88.8 | 8.5 | 0 |
| 100 | 76.5 | Toluene | 13.88 | 15 | 0.50 | 75.20 | 0.5 | 0.3 | 90 | 8.5 | 0 |
| 101 | 71.7 | Toluene/cyclohex | 20.00 | 25 | 1.00 | 59.12 | 0.6 | 0.6 | 87.6 | 9.4 | 0 |

TABLE II

| Exp. | Stg. Mtl. Str % | Solvent | Loading (%) | Filt. Temp. (°C.) | Stir Time (hr) | Recovery (%) | Total dinitro (%) | Isomer(3) (%) | Product (%) | 2'-nitro (%) | 6'-nitro (%) |
|---|---|---|---|---|---|---|---|---|---|---|---|
| 102 | 66.2 | 2-Chlorotoluene | 8.9 | 15 |  | 60.2 | 0 | 0.9 | 57 | 0.61 | 0.4 |
| 103 | 71.8 | 4-Chlorotoluene | 10 |  |  | 61.8 | 0 | 0.85 | 93.9 | 0 | 0 |
| 104 | 71.8 | 4-Chlorotoluene | 6.15 |  |  | 52.9 | 0.22 | 1.2 | 93.8 | 0.5 | 0.23 |
| 105 | 71.8 | 4-Chlorotoluene | 8.19 |  |  | 60 | 0 | 1.2 | 93.7 | 0.5 | 0.23 |
| 106 | 66.2 | 4-Chlorotoluene | 11.7 | 30 |  | 36.2 | 0 | 0.9 | 89.1 | 0.57 | 0.25 |
| 107 | 71.8 | 4-Chlorotoluene | 10.23 |  |  | 66.3 | 0 | 1.1 | 94.35 | 0.6 | 0.3 |
| 108 | 66.2 | 4-Chlorotoluene | 8.9 | 15 |  | 52.9 | 0 | 0.9 | 57.57 | 0.65 | 0.4 |
| 109 | 71.8 | 4-Chlorotoluene | 8 |  |  | 64.7 | 0 | 1.1 | 93.4 | 0.7 | 0.3 |
| 110 | 71 | 4-Chlorotoluene | 8.9 | 10 |  | 62.8 | 0 | 1.43 | 90.49 | 0.73 | 0.53 |
| 111 | 71.8 | 4-Chlorotoluene | 12.27 |  |  | 70.2 | 0 | 1.2 | 90 | 3.8 | 0.44 |
| 112 | 71.8 | 4-Chlorotoluene | 12 |  |  | 71.3 | 0 | 1 | 90.28 | 3.9 | 0.35 |
| 113 | 71.8 | 4-Chlorotoluene | 10 |  |  | 75.4 | 0 | 0.7 | 90.3 | 4.6 | 0.4 |
| 114 | 71.8 | 4-Chlorotoluene | 14.31 |  |  | 75.5 | 0 | 1.3 | 88.2 | 5.7 | 0.56 |
| 115 | 71.8 | 4-Chlorotoluene | 14 |  |  | 73.6 | 0 | 0.9 | 88.1 | 6.5 | 0.25 |
| 116 | 71.8 | 4-Chlorotoluene | 16.34 |  |  | 77.7 | 0 | 1.3 | 87.24 | 6.75 | 0.58 |
| 117 | 71.8 | 4-Chlorotoluene | 12 |  |  | 74.9 | 0 | 0.9 | 87.45 | 7.2 | 0.4 |
| 118 | 71.8 | 4-Chlorotoluene | 16 |  |  | 77.2 | 0 | 1 | 86.6 | 7.8 | 0.4 |
| 119 | 71.8 | 4-Chlorotoluene | 18 |  |  | 79.6 | 0 | 1.35 | 85.9 | 8.2 | 0.8 |
| 120 | 66.2 | Benzotrifluoride | 11.7 | 30 |  | 69.1 | 0 | 1.5 | 82.3 | 5.3 | 1.05 |
| 121 | 66.2 | Benzotrifluoride | 8.9 | 15 |  | 71.1 | 0 | 1.05 | 82.54 | 6.47 | 0.4 |
| 122 | 66.2 | Fluorobenzene | 11.7 | 21 |  | 31.2 | 0 | 1.42 | 87.17 | 1.05 | 0.52 |
| 123 | 66.2 | MCB | 8.9 | 15 |  | 28.4 | 0 | 1.4 | 88.7 | 0.8 | 0.38 |
| 124 | 66.2 | MCB | 11.7 | 30 |  | 30.3 | 0 | 1.21 | 86.56 | 0.91 | 0.52 |
| 125 | 71 | MCB | 8.9 | 0 |  | 61.3 | 0 | 1.66 | 89.8 | 1.17 | 0.7 |
| 126 | ? | o-xylene | 16 | 15 | 1 | 57.5 | 0.3 | 0.9 | 93.5 | 0.6 | 0.3 |
| 127 | ? | o-xylene | 18 | 15 | 1 | 74 | 0.3 | 1.4 | 87.9 | 4.1 | 0.4 |
| 128 | 66.2 | ODCB | 8.9 | 15 |  | 51.5 | 0 | 0.9 | 55.9 | 0.6 | 0.3 |
| 129 | 66.2 | Toluene | 8.9 | 15 | 2 | 38.1 | 0 | 1.3 | 85.6 | 1.4 | 0.7 |

TABLE III

| Exp. | Solvent | Loading Target % | Loading Act % | Filt Temp (°C.) | Stir time (hr) | Recovery (%) | loss (%) | Isomer(3) (%) | Product (%) | 2'-nitro (%) | 6'-nitro (%) |
|---|---|---|---|---|---|---|---|---|---|---|---|
| 130 | o-xylene | 16.00 | 16.35 | 15 | 1 | 19.16 | 72.79 | 0.9 | 94.7 | 0 | 0 |
| 131 | o-xylene | 20.06 | 20.56 | 15 | 2 | 37.22 | 52.20 | 0.8 | 96.1 | 0.2 | 0 |
| 132 | o-xylene | 16.00 |  | 15 | 1 | 39.55 | 48.04 | 0.8 | 94.15 | 0 | 0 |
| 133 | o-xylene | 20.00 | 20.71 | 15 | 2 | 45.81 | 42.47 | 0.9 | 98 | 0 | 0 |
| 134 | o-xylene | 16.00 |  | 15 | 1 | 48.97 | 43.01 | 0.8 | 96.65 | 0 | 0 |
| 135 | o-xylene | 20.00 | 20.47 | 15 | 1 | 49.27 | 43.70 | 0.9 | 95 | 0 | 0 |
| 136 | o-xylene | 16.00 | 16.34 | 15 | 1 | 49.91 | 39.91 | 0.9 | 94.6 | 0 | 0 |
| 137 | o-xylene | 19.99 | 20.98 | 15 | 1 | 52.72 | 38.22 | 0.7 | 97.5 | 0 | 0 |
| 138 | o-xylene | 16.00 |  | 15 | 1 | 52.92 | 37.75 | 0.7 | 94.5 | 0 | 0 |
| 139 | o-xylene | 15.97 | 16.13 | 15 | 1 | 53.37 | 42.58 | 0.8 | 94.9 | 0 | 0 |
| 140 | o-xylene | 19.98 | 21.15 | 15 | 1 | 56.46 | 31.86 | 0.7 | 95.5 | 0 | 0 |
| 141 | o-xylene | 18.00 |  | 25 | 1 | 56.53 | 0.00 | 1.45 | 95 | 0.3 | 0.1 |
| 142 | o-xylene | 17.81 | 18.40 | 15 | 1 | 64.50 | 30.28 | 0.6 | 94.1 | 0 | 0.1 |
| 143 | o-xylene | 18.07 | 18.52 | 15 | 1 | 66.71 | 28.69 | 0.7 | 95.3 | 0.8 | 0 |
| 144 | o-xylene | 15.09 |  | 10 | 1 | 67.02 | 27.36 | 1.1 | 96.4 | 0.3 | 0 |
| 145 | o-xylene | 15.09 |  | 15 | 1 | 67.80 | 49.81 | 0.8 | 96.15 | 0.8 | 0 |
| 146 | o-xylene | 18.11 |  | 25 | 1 | 68.12 | 0.00 | 0.8 | 88.7 | 5.1 | 0.2 |
| 147 | o-xylene | 16.60 |  | 15 | 4 | 68.19 | 32.78 | 1 | 90.35 | 5.8 | 0 |
| 148 | o-xylene | 15.09 |  | 15 | 4 | 69.15 | 0.00 | 0.7 | 89.65 | 6 | 0 |

TABLE III-continued

| | | Loading | | Filt Temp | Stir time | Recovery | | Product Analysis % w/w | | | |
|---|---|---|---|---|---|---|---|---|---|---|---|
| Exp. | Solvent | Target % | Act % | (° C.) | (hr) | (%) | loss (%) | Isomer(3) (%) | Product (%) | 2'-nitro (%) | 6'-nitro (%) |
| 149 | o-xylene | 20.00 | 20.15 | 15 | 2 | 69.96 | 22.23 | 0.6 | 89.15 | 6.45 | 0 |
| 150 | o-xylene | 16.60 | | 15 | 1 | 71.08 | 27.89 | 0.9 | 92.15 | 3.65 | 0 |
| 151 | o-xylene | 14.86 | | 15 | 1 | 73.29 | 21.22 | 0.6 | 90.6 | 4.3 | 0.1 |
| 152 | o-xylene | 16.60 | | 15 | 1 | 73.30 | 0.00 | 0.9 | 90.75 | 5.15 | 0.1 |
| 153 | ODCB | 18.00 | | 15 | 1 | 57.08 | 0.00 | 2.4 | 95.2 | 0.2 | 0.1 |
| 154 | p-xylene | 18.11 | | 25 | 1 | 59.95 | 36.79 | 0.9 | 90.1 | 5.1 | 0.1 |
| 155 | p-xylene | 15.09 | | 15 | 1 | 65.92 | 34.96 | 0.6 | 88.5 | 5.15 | 0 |
| 156 | p-xylene | 14.98 | | 15 | 4 | 78.06 | 21.37 | 0.9 | 87.9 | 7.9 | 0 |

TABLE IV

| Exp. | Stg Mtl. Str (%) | Solvent | Loading (%) | Filt Temp (° C.) | Stir Time (hr) | Recovery (%) | Product Analysis | | | |
|---|---|---|---|---|---|---|---|---|---|---|
| | | | | | | | Isomer(3) (%) | Product (%) | 2'-nitro (%) | 6'-nitro (%) |
| 157 | | 2-Chlorotoluene | 15 | 15 | 1 | 70 | 1 | 95.4 | 0 | 0.9 |
| 158 | | AcOH/water | | | | | 3 | 79.7 | 8.1 | 1.96 |
| 159 | 72.8 | AcOH/water | | | | 96 | 2.5 | 78.7 | 8.7 | 3.6 |
| 160 | 72.4 | AcOH/water | | | | 97.6 | 3.1 | 77.0 | 8.26 | 3.72 |
| 161 | | o-xyl/ODCB 95/5 | 20 | 25 | 1 | 60.6 | 0.8 | 92.5 | 1.6 | 0 |
| 162 | | o-xylene | 15 | 25 | 0.5 | 48.50 | 0 | 90.0 | 0 | 0 |
| 163 | | o-xylene | 15 | 25 | 1 | 55 | 0.72 | 98.1 | 0.48 | 0 |
| 164 | | o-xylene | 20 | 25 | 1 | 70.4 | 0.71 | 93.0 | 5.65 | 0.16 |
| 165 | 79.7 | o-xylene | 12 | 25 | 1 | 68.8 | 0.5 | 95.4 | 2.4 | 0 |
| 166 | 79.7 | o-xylene | 20 | | | 78.5 | 0.4 | 89.3 | 6.4 | 0 |
| 167 | | o-xylene | 25 | 25 | 0.5 | 88 | 0.6 | 91.2 | 6.7 | 0 |
| 168 | 78.7 | o-xylene | 15 | 25 | 1 | 73.8 | 0.4 | 91.4 | 5.95 | 0 |
| 169 | 78.7 | o-xylene | 12 | 25 | 1 | 68 | 0.3 | 90.7 | 5.2 | 0 |
| 170 | | o-xylene | 20 | 25 | 1 | 72.2 | 0.3 | 90.3 | 6.1 | 0 |
| 171 | | o-xylene | 20 | 25 | 1 | 88.7 | 0 | 89.5 | 5.7 | 0 |
| 172 | | o-xylene | 20 | 5 | 0.5 | 72.2 | 1.6 | 88.9 | 4.4 | 0.3 |
| 173 | | o-xylene | 12 | 5 | 1 | 61.3 | 1.3 | 94.1 | 0 | 0 |
| 174 | | o-xylene | 15 | 5 | 1 | 66 | 1.2 | 92.0 | 3.1 | 0 |
| 175 | | o-xylene | 20 | 25 | 0.5 | 83.6 | 0.6 | 90.8 | 6.5 | 0 |
| 176 | | o-xylene | 18 | 25 | 0.5 | 58 | 0.5 | 94.4 | 0 | 0 |
| 177 | | o-xylene | 15 | 25 | 1 | 77.7 | 0.5 | 94.4 | 3.7 | 0 |
| 178 | | o-xylene | 20 | 25 | 1 | 58 | 0.5 | 95.1 | 0 | 0 |
| 179 | | o-xylene | 18 | 25 | 1 | 54.3 | 0.5 | 94.9 | 0 | 0 |
| 180 | | o-xylene | 20 | 5 | 1 | 88.8 | 1.9 | 88.7 | 7.6 | 0 |
| 181 | | o-xylene | 30.8 | 5 | 1 | 83.8 | 1.7 | 87.6 | 6.4 | 0.1 |
| 182 | | o-xylene | 30 | 5 | 0.5 | 78.5 | 1.6 | 87.6 | 6.3 | 0.2 |
| 183 | | o-xylene | 18 | 5 | 1 | 68.1 | 1.5 | 89.2 | 5 | 0 |
| 184 | | o-xylene | 25.2 | 5 | 1 | 80.8 | 1.6 | 87.7 | 6.5 | 0 |
| 185 | | o-xylene | 20 | 5 | 1 | 74.6 | 1.5 | 87.5 | 5.9 | 0.3 |
| 186 | | o-xylene | 15 | 5 | 1 | 81.8 | 1.6 | 89.4 | 6.1 | 0 |
| 187 | | o-xylene | 12.2 | 5 | 1 | 77.7 | 1.5 | 90.8 | 4.5 | 0 |
| 188 | 20.4 | o-xylene | 21 | 4 | | 58 | 1.4 | 88.2 | 6.1 | 0.2 |
| 189 | 13.6 | o-xylene | 15 | 25 | | 51 | 0.7 | 95.7 | | |
| 190 | 13.6 | o-xylene | 15 | 25 | | 53 | 0.6 | 96.2 | | |
| 191 | 13.6 | o-xylene | 18 | 25 | | 64 | 0.6 | 96.5 | | |
| 192 | 13.6 | o-xylene | 21 | 25 | | 67.1 | 0.7 | 93.2 | 2.5 | |
| 193 | 13.6 | o-xylene | 18 | 25 | | 64 | 0.6 | 96.3 | 0 | |
| 194 | 13.6 | o-xylene | 15 | 25 | | 58 | 0.9 | 96.3 | 0 | |
| 195 | | ODCB | 16.5 | 15 | 1 | 76 | 0.6 | 96.8 | 0.45 | 0 |
| 196 | | ODCB | 18 | 15 | 1 | 83 | 0.7 | 95.1 | 1.5 | 0 |
| 197 | | ODCB | 20 | 15 | 1 | 79 | 0.6 | 90.6 | 5.4 | 0.15 |
| 198 | | ODCB | 18 | 15 | 1 | 76 | 0.6 | 91.2 | 3.75 | 0 |
| 199 | | ODCB | 18 | 15 | 2 | 74 | 0.9 | 91.1 | 2.4 | 0 |
| 200 | | ODCB | 18 | 15 | 1 | 82.7 | 0.7 | 94.1 | 4.9 | 0 |
| 201 | | ODCB | 18 | 15 | 6.25 | 82.7 | 0.7 | 90.1 | 8.42 | 0 |
| 202 | 78.7 | ODCB | 20 | 15 | 1 | 82 | 0.6 | 89.0 | 6.6 | 0 |
| 203 | | ODCB | 15 | 15 | 1 | 69.70 | 0.96 | 94.5 | 0 | 0 |
| 204 | | ODCB | 20 | 15 | | 77.4 | 0.7 | 93.8 | 3.1 | |
| 205 | 13.6 | ODCB | 15 | 15 | | 67 | 1.4 | 96.2 | 0 | |
| 206 | 13.6 | ODCB | 15 | 15 | | 75.5 | 1.3 | 96.5 | 0 | |
| 207 | 13.6 | ODCB | 15 | 15 | | 78.6 | 1.3 | 93.0 | 2.5 | |
| 208 | 62.8 | tech xylene | 11.8 | 30 | 4 | 40.1 | 0.3 | 89.4 | 0.96 | 0 |
| 209 | | tech-xylene | 17 | 30 | | 85.1 | 0.5 | 92.4 | 5.75 | |
| 210 | | tech-xylene | 17 | 19 | | 89.8 | 0.6 | 90.9 | 6.7 | |

TABLE IV-continued

| | Stg | | Filt | Stir | | Product Analysis | | | |
|---|---|---|---|---|---|---|---|---|---|
| Exp. | Mtl. Str (%) | Solvent | Loading (%) | Temp (° C.) | Time (hr) | Recovery (%) | Isomer(3) (%) | Product (%) | 2'-nitro (%) | 6'-nitro (%) |
| 211 | (67.9) | tech-xylene | 16.5 | 25 | 0.25 | 59 | 0.5 | 85.6 | 6.41 | 0 |
| 212 | (67.9) | tech-xylene | 15 | 30 | 4 | 55.8 | 0.4 | 86.5 | 5.3 | 0 |
| 213 | (62.8) | tech-xylene | 15 | 28 | 0.5 | 50.4 | 0.5 | 87.2 | 5.3 | 0 |
| 214 | (62.8) | tech-xylene | 15 | 26 | 0.75 | 51.2 | 0 | 79.1 | 4.4 | 0 |
| 215 | | tech-xylene | 12 | 25 | | 86.9 | 0.4 | 94.0 | 4.74 | 0 |
| 216 | | tech-xylene | 15 | 25 | 1 | 63 | 0.7 | 90.5 | 7.08 | 0 |
| 217 | | tech-xylene | 15 | 25 | 0.5 | 71.2 | 0 | 86.8 | 8.9 | 0 |
| 218 | 83.3 | tech-xylene | 25 | 25 | | 92 | 0.6 | 93.0 | 6 | |
| 219 | 13.6 | tech-xylene | 20 | | | 95.6 | 5.18 | 75.3 | 7.24 | 4.32 |
| 220 | 75.3 | tech-xylene | 20 | 25 | 0.5 | 68 | 0.6 | 90.7 | 8.6 | 0 |
| 221 | 13.6 | tech-xylene | 20 | | | 93.6 | 4.95 | 73.6 | 7.92 | 4.03 |
| 222 | 73.6 | tech-xylene | 20 | 25 | | 67.7 | 0.7 | 95.4 | 4.2 | 0 |
| 223 | 13.6 | tech-xylene | 20? | 25? | | 75.5 | 0.6 | 91.1 | 6 | 0 |
| 224 | | xyls/ACN95/5 | 17 | 25 | 1.5 | 22.2 | 0.4 | 92.4 | 1.1 | 0 |

The effectiveness of various crystallisation solvents can be seen from Tables I and II by a comparison of, for example, the results for Experiments Nos. 3, 11, 24, 31, 38, 41, 54, 60, 88 and 112 for which the solvents are 2-chlorotoluene, 2-fluorotoluene, benzotrifluoride, bromobenzene, monochlorobenzene, m-dichlorobenzene, o-xylene, o-dichlorobenzene, p-xylene and 4-chlorotoluene respectively. It can be seen that for all of these solvents it is possible to obtain the required product in a yield of between about 65% and 82% and at a purity of between about 81% and 96% depending upon the purity of the starting material and the crystallisation conditions employed. As briefly mentioned above, the proportion of the 2'-nitro isomer in the purified product is of critical importance since this is particularly difficult to separate from the required product and it can be seen from the experiments identified above that recrystallisation using o-xylene results in a particularly low content of the 2'-nitro isomer in the product mix. Other solvents which give low proportions of the 2'-nitro isomer include benzotrifluoride, monochlorobenzene and o-dichlorobenzene.

The beneficial effect of reduced loading of the crystallisation solution is apparent from the results presented in Tables I to IV. For example, in Table II, Experiments 104, 105, 107, 111, 114 and 116 all use 4-chlorotoluene as crystallisation solvents with loadings of 6.15, 8.19, 10.23, 12.27, 14.31 and 16.34 respectively. The yield of product increases as the loading increases from 52.9% at a loading of 6.15% to 77.7% at a loading of 16.34%. However, the purity of the product also decreases, particularly for loadings of greater than 10% and, in particular, the content in the product of the 2'-nitro isomer increases with loading. It is clear from the results shown for this series of experiments that the yield and product quality are optimised at a loading of between 8 and 12% when the crystallisation solvent is 4-chlorotoluene.

A similar effect can be seen from Table IV taking the results of Experiments 173 and 174 which both use o-xylene as solvent and have crystallisation solvent loadings of 12 and 15% respectively. Once again, it can be seen that, although the yield of product increases across this series from 61.3% to 66%, the purity of the product deteriorates from 94.1% to 92%. If these results are compared with those of Experiment 172, which was carried out under similar conditions except that the stir time was shorter, it can be seen that increasing the loading to 20% caused a decrease in the purity of the product and, in addition, an increase in the amount of 2'-nitro isomer from 0 to 4.4%. This shows that the increase in loading is significant because the shortened stir time tends to increase the quality of the product. Thus, for o-xylene, it appears that the optimum loading of the crystallisation solution is between about 12 and 15%.

The effect of loading is also demonstrated by taking the results of Experiments 195 to 197 of Table IV in which the solvent is o-dichlorobenzene. Here, the yield varies less than with some other solvents as the loading of the crystallisation solution is increased from 16.5 to 20% but the purity of the product is significantly affected, deteriorating from 96.8% to 90.6% with the amount of 2'-nitro isomer increasing from 0.45 to 5.4%. For this solvent, therefore, it would appear that the optimum crystallisation solution loading is between about 16 and 20%.

Thus, in summary, whatever the solvent, an increase in loading of the crystallisation solution always has the effect of decreasing the percentage of the required product and increasing the percentage of the 2'-nitro isomer in the final mixture obtained. This is significant because of the difficulty in separating the 2'-nitro isomer from the required 4'-nitro product. It is also clear that the optimum product loading may vary depending upon the particular crystallisation solvent which is used. In all cases, however, the loading of the crystallisation solvent should be kept below 25%.

Tables I to IV also demonstrate the effect of temperature on the purification process of the present invention. For example, in Table I, Experiments 25 and 26 were carried out in the same solvent, benzotrifluoride, and under similar conditions except that the filtration temperature was 15° C. for Experiment 25 and 10° C. for Experiment 26. Other groups of experiments which show the effect of a change in filtration temperature are Experiments 33 and 34, where the solvent was m-chlorobenzene, 54, 55 and 52 which used o-xylene as solvent, 86 and 88 using p-xylene; and 123 and 125 using m-chlorobenzene. In all of these groups of experiments except for the group using o-xylene as solvent, an increase in the filtration temperature led to a decrease in yield but also to a slight increase in the amount of 2'-nitro impurity present in the product. The results using o-xylene were particularly satisfactory because, with this solvent, a decrease in the filtration temperature used led not only to an increase in the product yield but also to a decrease in the amount of 2'-nitro impurity. Thus o-xylene is a particularly useful solvent for use in the process of the present invention.

The effect of prolonged stirring of the crystallisation mass can also be seen from Tables I to IV. In particular, Experiment 145 of Table 3 shows that after stirring for one hour a crystallisation mass in which the solvent is o-xylene and the filtration temperature is 15° C., a product of 96.15% purity containing 0.8% of the 2'-nitro isomer was obtained in 67% yield. However, when the same mixture was stirred for four hours (Experiment 148), the yield increased slightly to 69% but the product was only 89.65% pure and contained 6% of the 2'-nitro isomer.

EXAMPLE 3
Deposition of 2'-nitro Isomer from Recrystallisation Filtrates

Acifluorfen (19.4 g, 77% strength) was recrystallised from o-xylene to give a 63% recovery of acifluorfen of 91.3% strength and 5.1% 2'-nitro isomer content. On standing for several days, the filtrates deposited a solid which was recovered and analysed. The solid was 71.7% acifluorfen and 24% 2'-nitro isomer.

EXAMPLE 4
Telescoped Nitration and Purification Using 1,2-Dichlorobenzene

Crude 5-(2-chloro-α,α,α,-trifluoro-4-tolyloxy)benzoic acid (190 g, strength 84.2%), 1,2-dichloroethane (754 g) and acetic anhydride (87.8 g) were charged to a stirred reactor. The mixture was heated to 50° C. to produce a solution, then cooled to 10–15° C. Mixed acid (131 g, 33.3% nitric acid, 66.7% sulphuric acid) was added evenly over 2 hours at 10–15° C. After mixed acid addition, the reaction mass was held at 10° C. for 1 hour and then quenched with water (15 g). The mixture was heated to 70° C. and the acid layer was separated. The solvent layer was given two washes with 5% sodium chloride solution (210 g) at 70° C. to remove acetic acid. Water (194 g) was added and the 1,2-dichloroethane removed by distillation whilst returning the water phase to the reactor. To the resulting viscous oil/water mixture was added 1,2-dichlorobenzene (550 g) and the aqueous layer was separated off at 70° C. The solvent solution was given a water wash, separated and dried by azeotropic distillation. The resulting solution was cooled at 20° C. per hour to 15° C. and seeded with acifluorfen at 50° C. The crystallisation mass was stirred for 1 hour at 15° C., filtered and dried under reduced pressure before oven drying to remove residual solvent.

Yield of 5-(2-chloro-α,α,α,-trifluoro-4-tolyloxy)-2'-nitrobenzoic acid, 62.7% of theory.
The product had the following composition:
Acifluorfen 90.1%
2'-nitro 4.6%
6'-nitro 0.2%
others 2.6%

EXAMPLE 5
Effect of Stir Time on the Quality of Product From Recrystallisation of Acifluorfen The nitration, washing and solvent removal were carried out as in Example 4. o-Xylene (510 g) was added to the crude acifluorfen melt and the solution was dried and crystallised as in Example 4. Aliquots of about 130 g were removed from the crystallisation mass, after cooling to 15° C., at 1 hour intervals to determine the effect of stir time on product quality. The samples were filtered, pulled dry, oven dried and analysed and the results are shown in Table V below.

TABLE V

| Time at 15° C. | Acifluorfen strength % | 2'-nitro content % |
|---|---|---|
| 1 hour | 87 | 6.48 |
| 2 hour | 82.5 | 7.63 |
| 3 hour | 85.9 | 8.35 |
| 4 hour | 86.7 | 8.52 |
| 5 hour | 85.9 | 9.32 |
| 6 hour | 84.7 | 9.36 |

EXAMPLE 6
Telescoped Nitration and Purification Using o-Xylene

A solution of the sodium salt of crude 5-(2-chloro-α,α,α-trifluoro-4-tolyloxy)benzoic acid (433.2 g, strength 36.2%, expressed as free acid) and 1,2-dichloroethane (754 g) was charged to a stirred reactor and heated to 60° C. Sulphuric acid was added to adjust the pH to 2.0. The aqueous layer was separated and the solvent layer was dried by azeotropic distillation. Acetic anhydride (87.8 g) was added at 50° C. and the solution was nitrated and worked up to give the crude product as a molten oil/water mixture as in Example 4. To this mixture was added sodium hydroxide solution (60.9 g, 47% strength) at 50° C. to adjust the pH to >10. Traces of 1,2-dichloroethane were removed by distillation and o-xylene (833 g) was added followed by sulphuric acid (53 g) to adjust the pH to 2.0. After a short period of stirring, the aqueous layer was separated off whilst the mixture was at >70 ° C. The solvent layer was dried by azeotropic distillation, then cooled to 15° C. as described in Example 4. The acifluorfen product was recovered by filtration and dried.

Yield of 5-(2-chloro-α,α,α-trifluoro-4-tolyloxy)-2'-nitrobenzoic acid:
Nitration 83% theory
Recrystallisation 70.7% theory
Overall 58.8% theory.
The product had the following composition:
Acifluorfen 97.0%
2'-nitro 0.6%
6'-nitro 0.1%
Others 2.3%

EXAMPLE 7
Extraction of Crude Acifluorfen Acid with Aqueous Acetic Acid

Acifluorfen (21.7 g, 68.9% strength), acetic acid and water (10.9 g) were mixed and stirred at 22° C. for 2 hours. The slurry was filtered and the solid product given a small wash with 50% aqueous acetic acid. The product was oven dried at 80° C. The recovery of acifluorfen was 95.9% and the product had an acifluorfen strength of 79.2%.

EXAMPLE 8
Acifluorfen Acid Washing and Recrystallisation Procedure
1. First Wash o-Xylene (263 g), concentrated HCl (16 g) and crude acifluorfen sodium salt solution (116 g, 39.3% strength) were mixed and heated to 80° C. The pH of the aqueous phase was adjusted, if necessary, to pH 1 or less with a further addition of concentrated HCl. The resulting mixture was agitated for 15 min then allowed to separate. The lower aqueous phase was then removed.

2. Subsequent Washes

Water (65 g) was added to the organic phase and the mixture agitated and reheated to 80° C. The pH of the mixture was then adjusted to the target value by addition of concentrated HCl or 25% sodium hydroxide solution. The mixture was agitated at the target pH for 15 min then allowed to separate for 15 min before removal of the aqueous layer. This procedure was repeated as indicated in Tables VI and VII. After washing, the organic phase was cooled to 50° C. at a rate of 20° C./hour with seeding at 50° C. and 45° C., then held at 5° C. for 1 hour. The purified acifluorfen was filtered off, washed with chilled o-xylene (25 g) and the wet cake dried in a vacuum oven.

The results of various washing procedures performed in this manner are illustrated in Tables VI and VII below.

TABLE VI

| No of first washes at pH 1.0 | No of subsequent washes at controlled pH (and pH value) | Product Str. % | 2'-Nitro % | Yield % |
|---|---|---|---|---|
| 2 | 0 | 95.2 | 0.21 | 64 |
| 4 | 0 | 95.9 | 0.13 | 64.8 |
| 1 | 1 (pH 3.3) | 94.8 | 0.1 | 69.8 |
| 1 | 2 (pH 3.3) | 94.6 | 1.36 | 74.6 |
| 1 | 2 (pH 3.5) | 93.2 | 3.3 | 77.1 |
| 1 | 3 (pH 3.3) | 90.4 | 5.64 | 80.8 |
| 1 | 1 (pH 4.0) | 96.3 | 0 | 49.4 |

TABLE VII

| | Average results | | | |
|---|---|---|---|---|
| First wash pH | Second wash pH | Third wash pH | Product Str. % | 2'-Nitro % | Yield % |
| 3.5 | 3.5 | — | 96.5 | — | 54 |
| 4.0 | 1.0 | — | 94.7 | 0 | 61.6 |
| 3.5 | 3.5 | 1.0 | 95.5 | 0 | 64 |
| 1.0 | 4.0 | 1.0 | 94 | 0.2 | 70.5 |
| 1.0 | 3.8 | 1.0 | 95.5 | 0.7 | 74.5 |

EXAMPLE 9

A. Purification of Acifluorfen Acid Using Acid Washes Without Back Extraction

Step 1. o-Xylene (195 g), 36% HCl (17.3 g), and 99.5 g and crude acifluorfen sodium salt solution (99.5 g 40.26% strength) were mixed in a 1 litre reactor and heated to 80° C. The pH of the aqueous phase was adjusted if necessary to be <1 with the further addition of HCl. After settling the lower aqueous phase was removed.

Step 2. Water (98 g) was added to the organic phase and 25% NaOH (3 g) was added. After heating to 80° C. the pH was adjusted to 3.8–4.0, by the addition of further NaOH if necessary. After settling the lower aqueous phase was removed.

Step 3. Water (98 g) was added to the organic phase for the second wash (a small charge of NaOH was added if necessary to adjust the pH of the mixture to 3.8–4.0) and heated to 80° C. After settling the lower aqueous phase was removed.

Step 4. Water (33 g) and 98% $H_2SO_4$ (2 g) were added to the organic phase to bring the pH below 2 and the mixture heated to 80° C. After settling the lower aqueous phase was removed.

Step 5. Fresh o-Xylene (32 g) was added to bring the acifluorfen acid loading in xylene to 15%.

Step 6. The mixture was cooled to 5° C. During cooling, seeding with pure acifluorfen was begun at about 45° C. The slurry was held at 5° C. for 0.5 to 1 hour and then filtered and dried under reduced pressure.

B. Purification of Acifluorfen Acid Using Acid Washes and Back Extraction

Step 1. The first two water washes from a double wash acifluorfen acid purification run were taken and fresh o-xylene (195 g) was added and the mixture heated to 80° C.

Step 2. The pH of the mixture was adjusted to about 3.6 by adding 10% HCl (1.3 g).

Step 3. After settling the lower aqueous phase was removed and the xylene layer which contains the recovered acifluorfen acid is recycled to the purification process described in A, step 1 bove.

The results of these washing procedures are set out in Table VIII below.

TABLE VIII

| | | Quality | |
|---|---|---|---|
| Process Used | Yield % | AA Str. % | 2'-nitro % |
| Double pH adjusted wash, no back extraction | 77 | 93.7 | 3.1 |
| Double pH adjusted wash, with back extraction | 81.9 | 95.1 | 1.7 |

We claim:
1. A process for the purification of a compound of general formula I:

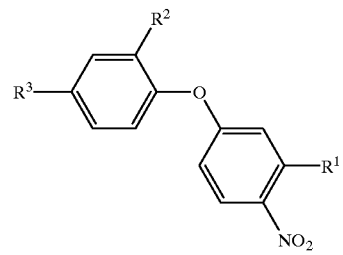

wherein $R^1$ is hydrogen or $C_1$–$C_6$ alkyl, $C_2$–$C_6$ alkenyl or $C_2$–$C_6$ alkynyl, any of which may optionally be substituted with one or more substituents selected from halogen and hydroxy; or $COOR^4$, $COR^6$, $CONR^4R^5$ or $CONHSO_2R^4$;

$R^4$ and $R^5$ independently represent hydrogen or $C_1$–$C_4$ alkyl optionally substituted with one or more halogen atoms;

$R^6$ is a halogen atom or a group $R^4$;

$R^2$ is hydrogen or halo; and $R^3$ is $C_1$–$C_4$ alkyl, $C_2$–$C_4$ alkenyl or $C_2$–$C_4$ alkynyl, any of which may optionally be substituted with one or more halogen atoms; or halo;

or, where appropriate, a salt thereof;

from a mixture containing the compound of general formula I together with one or more isomers or di-nitrated analogues thereof; the process comprising dissolving the mixture in a suitable crystallising solvent selected from an aromatic hydrocarbon, a haloaromatic, a mixture of any of the above solvents or a mixture containing an aromatic hydrocarbon with a co-solvent comprising an aliphatic hydrocarbon, ester, ether, nitrile or a halohydrocarbon and recrystallising the product from the resulting crystallisation solution wherein the crystallisation solution contains not more than 25% loading of the compound of general formula I and the temperature to which the solution is cooled for crystallisation is not greater than about 30° C.; wherein, after the addition of the crystallising solvent but before recrystallisation, the crystallisation solution is subjected to at least one wash with an aqueous solution having an acid pH.

2. A process as claimed in claim 1, which includes up to five aqueous washes at an acid pH.

3. A process as claimed in claim 1, wherein the crystallisation solution is washed with an aqueous solution having a pH of from 3 to 3.8.

4. A process as claimed in claim 3, wherein the crystallisation solution is washed with an aqueous solution having a pH of from 3.3 to 3.5.

5. A process as claimed in claim 1, wherein the crystallisation solution is washed with an aqueous solution having a pH of between 3.0 and 4.5, followed by an additional wash at a pH of <2.0.

6. A process as claimed in claim 1, which includes a first wash at pH <2.0, followed by one to three washes at a pH of 3.0 to 4.5, followed by a final wash at pH <2.0.

7. A process for the purification of a compound of general formula I:

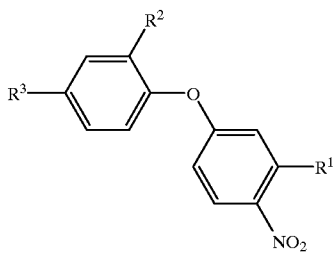

wherein R1 is hydrogen or C1–C6 alkyl, C2–C6 alkenyl or C2–C6 alkynyl, any of which may optionally be substituted with one or more substituents selected from halogen and hydroxy; or COOR4, COR6, CONR4R5 or CONHSO2R4;

R4 and R5 independently represent hydrogen or C1–C4 alkyl optionally substituted with one or more halogen atoms;

$R^6$ is a halogen atom or a group $R^4$;

$R^2$ is hydrogen or halo; and

R3 is C1–C4 alkyl, C2–C4 alkenyl or C2–C4 alkynyl, any of which may optionally be substituted with one or more halogen atoms; or halo;

or, where appropriate, a salt thereof;

from a mixture containing the compound of general formula I together with one or more isomers or di-nitrated analogues thereof; the process comprising dissolving the mixture in a suitable crystallising solvent selected from an aromatic hydrocarbon, a haloaromatic, a mixture of any of the above solvents or a mixture containing an aromatic hydrocarbon with a co-solvent comprising an aliphatic hydrocarbon, ester, ether, nitrile or a halohydrocarbon and recrystallising the product from the resulting crystallisation solution wherein the crystallisation solution contains not more than 25% loading of the compound of general formula I and the temperature to which the solution is cooled for crystallisation is not greater than about 30° C.; wherein, after the addition of the crystallising solvent but before recrystallisation, the crystallisation solution is subjected to at least one wash with an aqueous solution having an acid pH and the aqueous wash is back extracted with fresh crystallising solvent.

8. A process according to claim 7 wherein the crystallising solvent is recycled into the crystallisation process.

9. A process according to claim 7 in which the washings from multiple pH controlled washes are combined prior to back-extraction.

10. A process for the partial purification of a product mixture obtained from the nitration of a compound of general formula II to give a compound of general formula I, the process comprising removing the reaction solvent and treating the resultant crude product with a mixture of water and a water-miscible polar solvent.

11. A process as claimed in claim 10, wherein any acetic anhydride in the crude product is hydrolysed with water to give acetic acid and this, or acetic acid from any other source, is left in the reaction mass to act as the polar solvent.

12. A process as claimed in claim 10, wherein the crude product of the nitration reaction, after washing and removal of the reaction solvent, is treated with a mixture of a polar solvent and water to achieve partial dissolution of impurities and isomers without substantial loss of the desired product which can then be recovered by filtration.

13. A process as claimed in claim 10, wherein the polar solvent is formic acid, acetic acid, propionic acid, methanol, acetonitrile or acetone.

14. A process as claimed in claim 10, wherein the proportion of polar solvent to water is in the range of from about 3:7 to 7:3 and the amount of crude nitrated isomer mixture in the polar solvent/water solution is from about 20 to 80% by weight.

15. A process as claimed in claim 10 followed by a process as claimed in claim 15.

16. A process as claimed in claim 10, wherein the compound of general formula I is 5-(2-chloro-α,α,α-trifluoro-4-tolyloxy)-2'-nitrobenzoic acid (acifluorfen) or 5-(2-chloro-α,α,α-trifluoro-4-tolyloxy)-N-methanesulfonyl-2'-nitro-benzamide (fomesafen).

17. A process as claimed in claim 16, wherein the compound of general formula I is acifluorfen and the process further comprises converting the acifluorfen to its acid chloride and reacting the acid chloride with methane sulfonamide to give fomesafen.

18. A process according to claim 17 wherein the acifluorfen is prepared by a process comprising the steps of:
 a) reacting m-cresol with DCBTF to produce 3-(2-chloro-α,α,α-trifluoro-4-tolyloxy)toluene;
 b) oxidising 3-(2-chloro-α,α,α-trifluoro-4-tolyloxy) toluene to give 3-(2-chloro-α,α,α-trifluoro-4-tolyloxy) benzoic acid; and
 c) nitrating 3-(2-chloro-α,α,α-trifluoro-4-tolyloxy) benzoic acid to give acifluorfen.

19. A process as claimed in claim 10, wherein the compound of general formula I is 5-(2-chloro-α,α,α-trifluro-4-tolyloxy)-2'-nitrobenzoic acid (acifluorfen) or 5-(2-chloro-α,α,α-trifluoro-4-tolyloxy)-N-methanesulfonyl-2-nitrobenzamide (fomesafen).

20. A process as claimed in claim 1, wherein the crystallisation solvent is o-xylene.

21. A process as claimed in claim 1, wherein the loading of the crystallisation solution is from about 8% to 20%.

22. A process as claimed in claim 1, wherein the temperature to which the solution is cooled to effect crystallisation is not greater than 20° C.

23. A process as claimed in claim 1, wherein, after crystallisation, the mixture is allowed to stand for no more than about four hours before recovery of the product.

24. A process as claimed in claim 1, wherein the mixture to be purified is the crude product of a process for the nitration of a compound of general formula II:

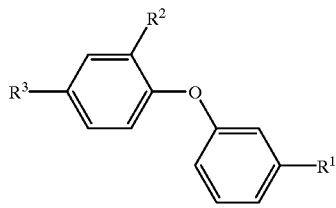

wherein $R^1$, $R^2$ and $R^3$ are as defined for general formula I.

25. A process as claimed in claim 24, wherein the nitration agent is nitric acid or a mixture of nitric and sulfuric acids and in which the reaction takes place in the presence of from 1 to 3 moles of acetic anhydride per mole of compound of general formula II and at a temperature of from about −15° C. to 15° C.

26. A process as claimed in claim 15, wherein the crystallisation solvent is o-xylene.

27. A process as claimed in claim 15, wherein the loading of the crystallisation solution is from about 8% to 20%.

28. A process as claimed in claim 15, wherein the temperature to which the solution is cooled to effect crystallisation is not greater than 20° C.

29. A process as claimed in claim 15, wherein, after crystallisation, the mixture is allowed to stand for no more than about four hours before recovery of the product.

30. A process as claimed in claim 15, wherein the mixture to be purified is the crude product of a process for the nitration of a compound of general formula II:

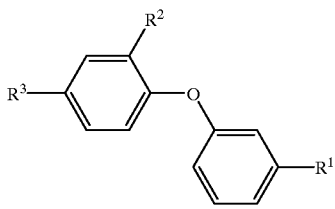

wherein $R^1$, $R^2$ and $R^3$ are as defined for general formula I.

31. A process as claimed in claim 30, wherein the nitration agent is nitric acid or a mixture of nitric and sulfuric acids and in which the reaction takes place in the presence of from 1 to 3 moles of acetic anhydride per mole of compound of general formula II and at a temperature of from about −15° C. to 15° C.

* * * * *